United States Patent
Hofmann et al.

[11] Patent Number: 6,027,488
[45] Date of Patent: Feb. 22, 2000

[54] FLOW-THROUGH ELECTROPORATION SYSTEM FOR EX VIVO GENE THERAPY

[75] Inventors: Gunter A. Hofmann, San Diego; Dietmar Rabussay, Solana Beach, both of Calif.

[73] Assignee: Genetronics, Inc., San Diego, Calif.

[21] Appl. No.: 09/090,471

[22] Filed: Jun. 3, 1998

[51] Int. Cl.[7] .................. A61M 37/00; A61M 31/00; C12N 13/00
[52] U.S. Cl. ................ 604/522; 435/173.6; 604/4
[58] Field of Search ................ 604/4, 7, 19–21, 604/500, 522; 128/898; 607/148; 435/173.6

[56] References Cited

U.S. PATENT DOCUMENTS

| | | | |
|---|---|---|---|
| 5,545,130 | 8/1996 | Hofmann et al. | 604/4 |
| 5,612,207 | 3/1997 | Nicolau et al. | 435/173.6 |
| 5,676,646 | 10/1997 | Hofmann et al. | 604/4 |
| 5,702,359 | 12/1997 | Hofmann et al. | 604/20 |
| 5,729,201 | 3/1998 | Meserol | 422/44 |

*Primary Examiner*—Corrine McDermott
*Assistant Examiner*—Michael J. Hayes
*Attorney, Agent, or Firm*—Gray Cary Ware & Freidenrich LLP; Lisa A. Haile

[57] ABSTRACT

A method and apparatus for introducing a preselected molecule into a living cell by contacting the cell with the preselected molecule and applying a multiple series of electrical pulses to the cell. The method can be utilized ex vivo. The multiple electrical pulses generate rotating electric fields which introduce transient pores in the living cell without killing the cell. The rotating electric fields are provided in a flow through chamber apparatus having more than two electrodes. A three-step pulse process, e.g. collection, electroporation, electrophoresis, is used to introduce the preselected molecule into the cell. A mechanical means of repositioning cells between successive pulses is also provided. The apparatus can also provide a means to pulse cells at different temperatures and then after pulsing, let the cells recover for a specified residence time at another temperature.

34 Claims, 9 Drawing Sheets

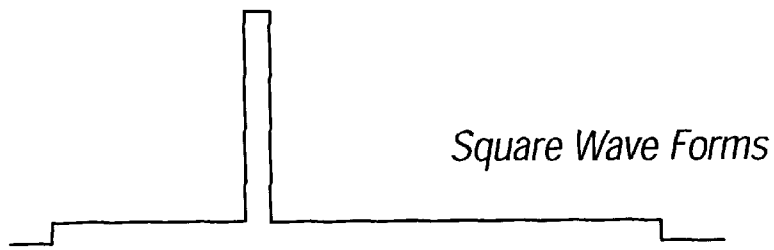
FIG. 3C — Square Wave Forms
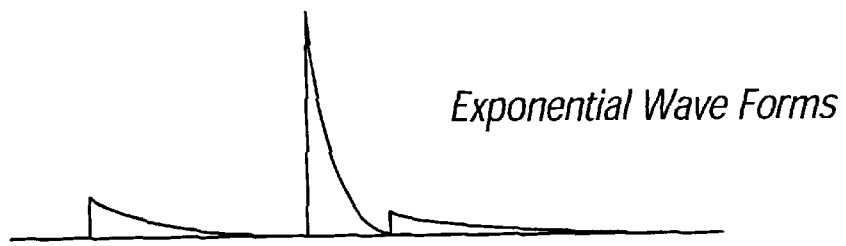
FIG. 3D — Exponential Wave Forms
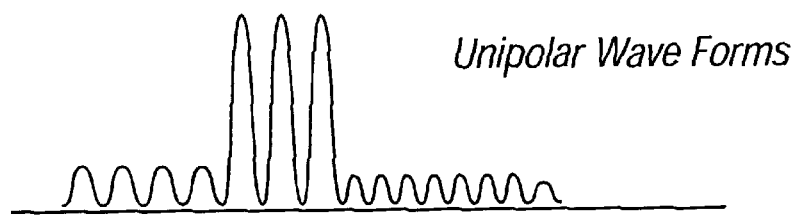
FIG. 3E — Unipolar Wave Forms
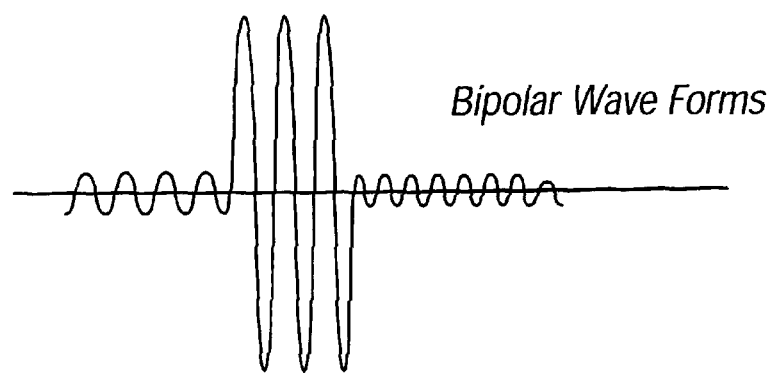
FIG. 3F — Bipolar Wave Forms

FLOW-THROUGH ELECTROPORATION SYSTEM FOR EX VIVO GENE THERAPY

FIELD OF THE INVENTION

The present invention relates generally to the use of electric pulses to increase the permeability of a cell and more specifically to a flow-through electroporation system.

BACKGROUND OF THE INVENTION

Electric fields can be used to create pores in cells without causing permanent damage. This allows for insertion of large molecules into cell cytoplasm. Genes and other molecules such as pharmacological compounds can be incorporated into live cells through a process known as electroporation. The genes or other molecules are mixed with the live cells in a buffer medium. Short pulses of high electric fields are applied to make the cell membranes transiently porous so that the genes or molecules can enter the cells and modify the genome of the cells.

Studies have shown that large size nucleotide sequences (e.g., up to 630 kb) can be introduced into mammalian cells via electroporation (Eanault, et al., Gene (Amsterdam), 144(2):205, 1994; Nucleic Acids Research, 15(3):1311, 1987; Knutson, et al., Anal. Biochem., 164:44, 1987; Gibson, et al., EMBO J., 6(8):2457, 1987; Dower, et al., Genetic Engineering, 12:275, 1990; Mozo, et al., Plant Molecular Biology, 16:917, 1991). However, the efficiency of electroporation, as reflected in the current literature, is usually low (see U.S. Pat. No. 5,019,034, herein incorporated by reference). A typical result is from about 5 to 20 percent transfection depending on conditions, parameters and cell type. Creation of a high efficiency method and apparatus for the of transfer of nucleic acid and the introduction of other preselected molecules into living cells via electroporation is desired.

Genetronics, Inc, San Diego, Calif., has provided an ex vivo flow through electroporation method and chamber in U.S. Pat. Nos. 5,676,646 and 5,545,130, the disclosures of which are incorporated herein by reference.

SUMMARY OF THE INVENTION

The present invention provides a method and an apparatus for introducing preselected molecules into a living cell by contacting the cell with the preselected molecules and electrically applying a multiple series of three-step pulses to the cell. The method can be utilized ex vivo.

A three-step pulse process having steps of collection, electroporation, electrophoresis can be used to introduce preselected molecules into the cell. Each three-step pulse includes three discrete electrical impulses each having a specified duration and strength to achieve its respective function.

Each three-step pulse generates an electrical field with a particular field orientation within a flow through chamber apparatus. A rotating electric field can be generated by applying multiple three-step pulses with each three-step pulse having an electric field in a different orientation. This rotating electric field can be configured to introduce transient pores in the living cell without killing the cell. The rotating electric field is provided in a flow through chamber apparatus having more than two electrodes.

A mechanical means of repositioning cells between successive pulses is also provided, e.g., a vibrating table for agitating the cell-molecule mixture. This can increase the areas of permeabiliztion of the living cells.

An apparatus in accordance with the invention can also provide a means to pulse cells at different temperatures and then after pulsing, let the cells recover for a specified residence time at another temperature.

The use of such features provides high viability of cells after electroporation and high transformation efficiency.

These and other aspects and advantages of the invention will become more apparent in light of the following drawings, detailed description and the appended claims.

BRIEF DESCRIPTION OF THE DRAWINGS

FIGS. 3C–3F illustrate several three-step pulse waveforms.

DESCRIPTION OF THE PREFERRED EMBODIMENTS

Figure 1:
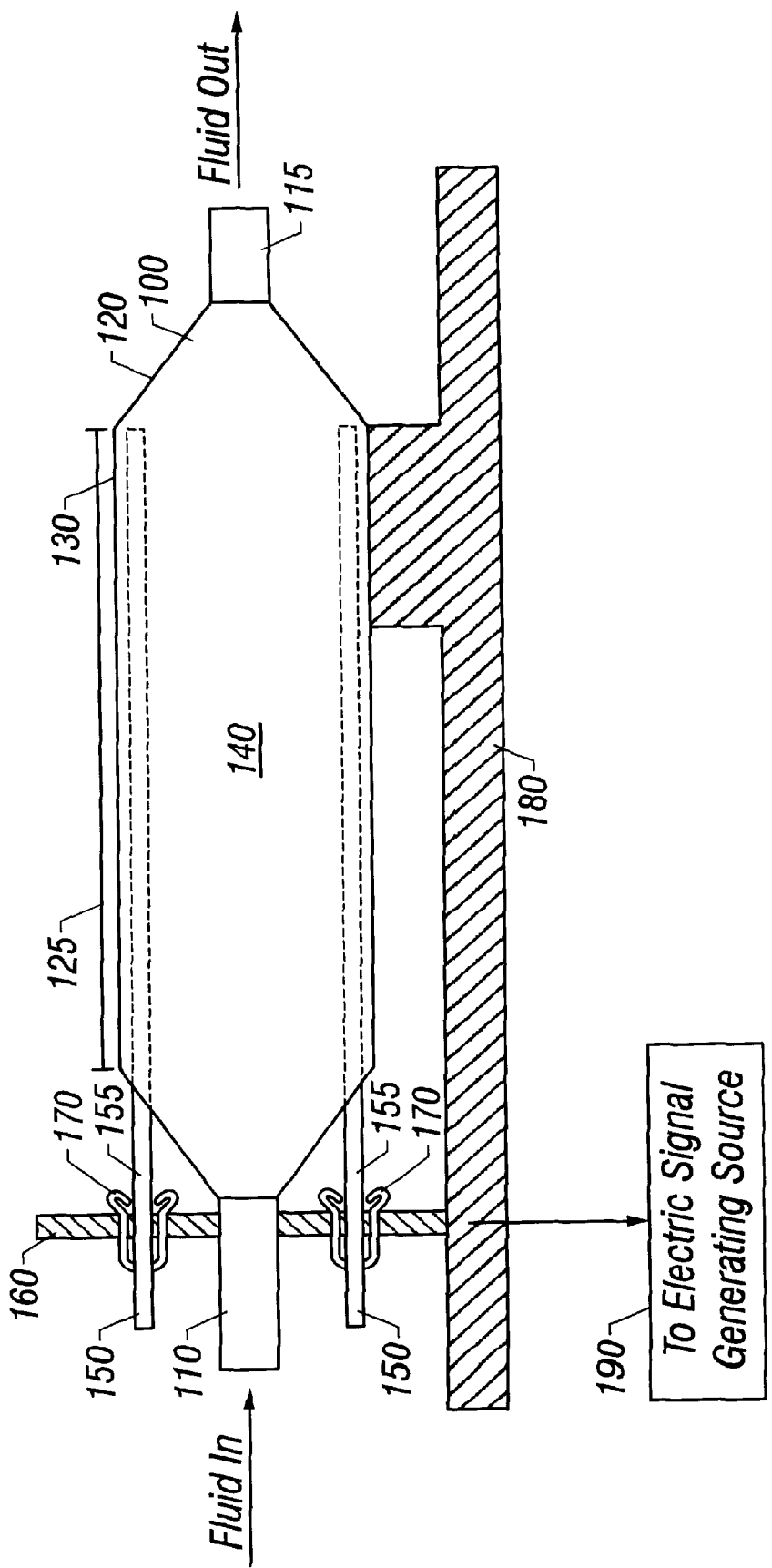
FIG. 1 is schematic showing a sectional view through a coaxial flow through chamber for generating rotating electric fields.

FIG. 1 shows a sectional view through a flow through chamber 100 for generating rotating electric fields according to one embodiment of the invention. A housing 120 is provided, having walls 130 to define an elongated internal chamber 140 which extends the length 125 of the housing 120. An inlet 110 and an outlet 115 are connected to the internal chamber 140 to provide a conduit for continuous or pulsating fluid flow along the length 125 of the internal chamber 140.

More than two electrodes 150 are positioned within the housing 120 and in contact with the internal chamber 140. Each of the electrodes 150 has a section 155 that extends outside the housing 120. This section 155 of the electrode 150 is preferably inserted into a printed circuit board template 160 and held in place by detachable electrical contacts 170 such as sliding contacts as shown. The sliding contacts 170 provide easy removal and insertion of the flow through chamber 100. The flow through chamber 100 can be disposable or removed from the circuit board template 160 for sterilization. The circuit board template 160 is supported by a support structure 180. The electrodes 150 are thus electrically connected to the circuitry in the circuit board template 160. The circuit board template 160 is electrically connected to an electrical signal generating source 190.

Figure 2A:
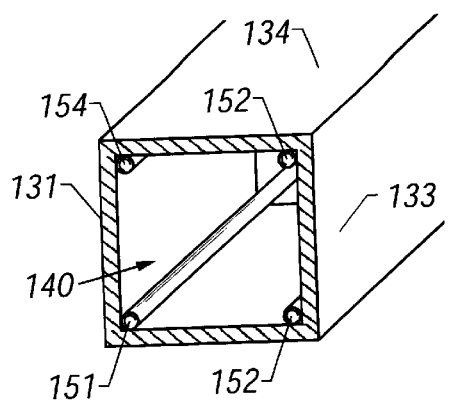
FIG. 2A is a schematic showing an end view of a square housing utilized in the flow through chamber illustrated in FIG. 1.

More than two electrodes 150 are incorporated into the housing of the flow through chamber 100 in order to generate rotating electric fields in the internal chamber 140. Applying rotating electric fields to living cells for electroporation can effectively increase preselected molecule uptake and efficacy. Certain aspects of using rotating electric fields to enhance electroporation are described in U.S. Pat. No. 5,702,359, which is incorporated herein by reference. The electrodes 150 are formed of electrically conducting materials and may be gold plated. In one implementation, the electrodes 150 can be linear rods spaced apart and disposed at the place where one wall 131 meets an adjacent wall 132 of the housing 120 along the length 125 of the housing 120 as shown in FIGS. 2A and 2C. The shape and the number of walls of the housing can be modified to accommodate various numbers of linear rod electrodes. A circular cylindrical housing, for example, is anticipated. Two particular configurations of the housing 120 are illustrated in FIGS. 2A and 2C.

FIG. 2A shows an end view of a square housing utilized in a flow through chamber illustrated in FIG. 1. The housing 120 has four walls 131, 132, 133, 134 which define a square elongated internal chamber 140. The four linear electrodes 151, 152, 153, 154 are spaced apart and positioned within the housing 120. Each electrode 151 is positioned along the length of an intersection between one wall 131 and an adjacent wall 132.

The four electrodes 151, 152, 153, 154 in the square housing 120 are each connected to the electrical signal generating source 190 via the printed circuit board template 160. The electrical signal generating source 190 provides pulsed electrical fields to two opposing pairs of electrodes so that electrical fields are respectively established between electrodes 151, 152, 153, and 154. Each pulse can have a three-step wave form, called a three-step pulse illustrated in FIGS. 3A–3B. The electric field can be rotated between each successive three-step pulse, however, the electric field is not rotated in between each impulse step of the three-step pulse. After one or several pulses, a pulse generator control 197 in the electrical signal generating source 190 connects another pair of electrodes in the square housing 120 which are positioned 90 degrees from the first set up and pulses again. This enables each successive electric pulse to generate a different electric field configuration which ultimately produces a rotating electric field within the elongated internal chamber 140.

Figure 2B:
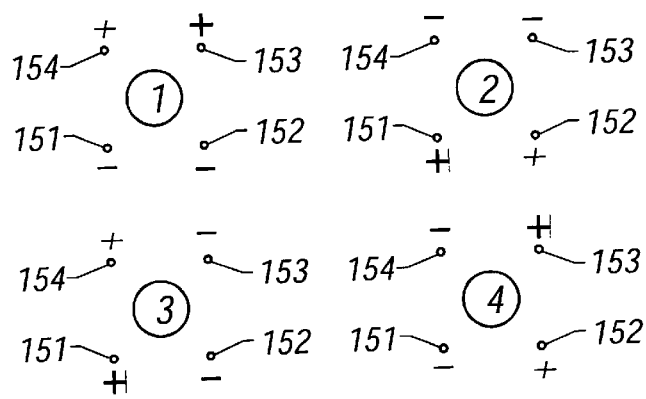
FIG. 2B is a diagram illustrating four possible electric field configurations generated by a flow through chamber having the square housing illustrated in FIG. 2A.
Figure 2C:
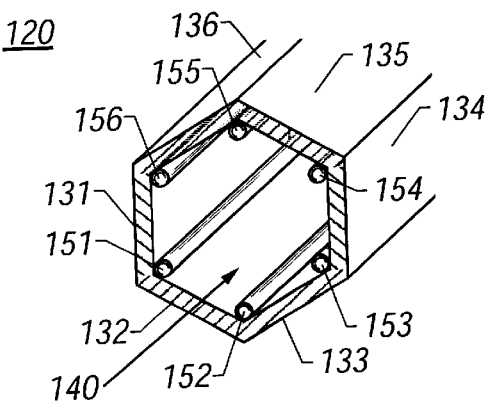
FIG. 2C is a diagram showing an end view of a hexagonal housing utilized in the flow through chamber illustrated in FIG. 1.

The four electrodes are capable of generating four different electric field configurations as shown in FIG. 2B. In the first configuration, electrodes 151 and 152 are connected together and electrodes 153 and 154 are connected together. In the second configuration, like the first configuration, the same pairs of electrodes are connected together but the opposite charge is imposed on the electrodes. In the third configuration, electrodes 151 and 154 are connected together and electrodes 152 and 153 are connected together. In the fourth configuration, like the third configuration, the same pairs of electrodes are connected together but the opposite charge is imposed on the electrodes. Changing the connections of the electrodes changes the configuration and orientation of the electrical field and generates a rotating electric field. The pulse generator control 197 can be programed to rotate the electric field automatically or alternatively, the pulse generator control 197 can be operated manually.

Figure 2D:
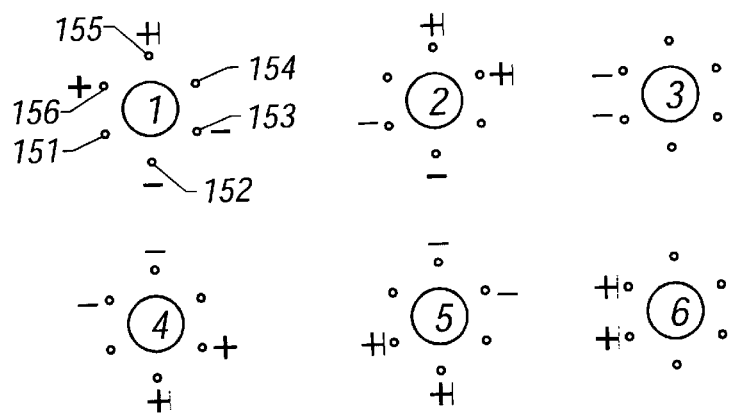
FIG. 2D is a diagram illustrating six possible electric field configurations generated by a flow through chamber having the hexagonal housing illustrated in FIG. 2C.

FIG. 2C is an end view of a hexagonal housing utilized in a flow through chamber illustrated in FIG. 1. The housing 120 has six walls 131, 132, 133, 134, 135, 136 which define a hexagonal elongated internal chamber 140. The six linear electrodes 151, 152, 153, 154, 155, 156 are spaced apart and positioned within the housing 120. The six electrodes are capable of generating six different electric field configurations as shown in FIG. 2D.

To introduce preselected molecules into living cells, a liquid cell sample and a fluid medium having preselected molecules are combined to form a liquid cell-molecule mixture. This mixture is then feed into the internal chamber 140 of the flow through chamber 100 via inlet 110. Inside the internal chamber 140, the cells in the mixture are exposed to rotating electric fields generated by the electrodes 150.

Figure 3A:
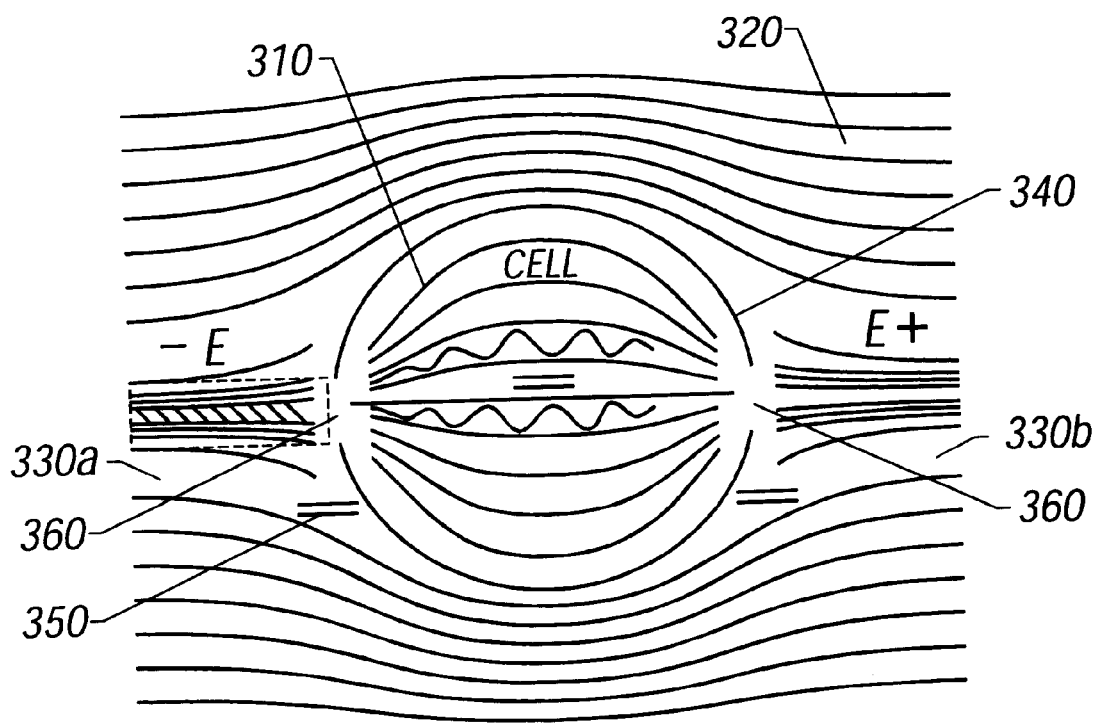
FIG. 3A is an illustration of a cell in an electric field E undergoing a three step process, e.g. collection, electroporation, and electrophoresis, for introducing preselected molecules into the cell.
Figure 3B:
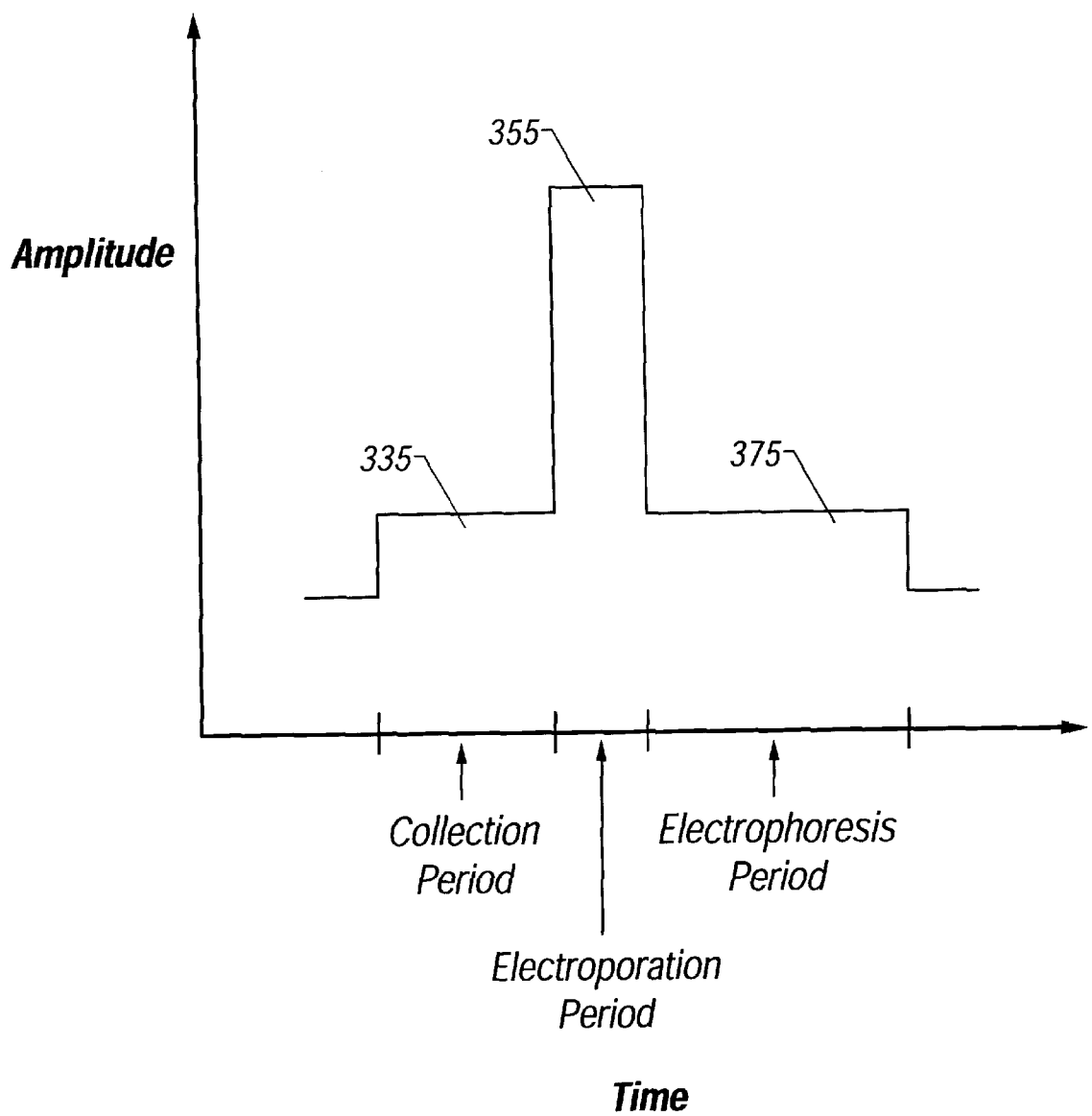
FIG. 3B shows relative electric pulse amplitude and duration for the three step process illustrated in FIG. 3A.

FIGS. 3A–3B illustrate a three-step pulse process, e.g. collection, electroporation, electrophoresis, which is used to introduce preselected molecules into the cell. Each three-step pulse includes three discrete electrical impulses having a specified duration and strength to achieve its respective function. FIG. 3A shows a cell 310 in an electric field 320. In the collection step, a first electric impulse 335 is applied to collect charged preselected molecules at regions 330$a$, 330$b$ near the cell membrane 340. Next in the electroporation step, a second electric impulse 355 is applied to permeabilize the cell membrane 340 forming transient pores 360. Finally in the electrophoresis step, a third electric impulse 375 is applied to transport the preselected molecules through the transient pores 360 into the cell 310.

FIG. 3B shows the relative amplitude and duration of each electric impulse in a single three-step pulse. The collection impulse 335 and the electrophoresis impulse 375 may have similar amplitudes while the amplitude of the electroporation impulse 355 can be significantly larger than that of the other two impulses. The amplitude of the electroporation impulse 355 is sufficient to cause transient pores 360 in the cell membrane 340. Preferably, the electroporation impulse 355 creates an electric field of about 100 to 10,000 Volts per centimeter. Since the collection step and the electrophoresis step does not function to create additional membrane permeabilization, the amplitude of the collection impulse 335 and the electrophoresis impulse 375 is much lower than the amplitude of the electroporation impulse 355. Preferably the collection impulse 335 and the electrophoresis impulse 375 each create an electric field of about 10 to 1000 Volts per centimeter.

The time duration of the high amplitude impulse 355 is shorter than that of the other two impulses 335, 375 because a long exposure of a living cell to the high amplitude impulse 335 may damage or even kill the living cell. Preferred time duration ranges for each pulse are as follows: the collection impulse 335 is about 0.1 to about 1000 ms; the electroporation impulse 355 is about 1 to about 1000 $\mu$s; the electrophoresis impulse 375 is about 0.1 to about 1000 ms. The long pulse length of the electrophoresis pulse 375 allows the preselected molecules to be "loaded" into the opened pores via an electrophoretic event and increases the number of molecules delivered to each cell. Thus a higher percentage of cells is transfected. Also, the cells can be placed into a bath to allow longer recovery time after the three-step pulse has been applied.

Certain selected molecules may be charged with either positive or negative polarity. For positively charged particles, for example, only the molecules initially located between a target cell and the positive electrode may migrate to the region 330a near the cell membrane 340 and to enter the cell. For positively charged molecules that are initially located between the target cell and the negative electrode, the electric field forces those molecules to move away from the cell membrane 340. Hence, in order to improve the efficiency of electroporation, the target cells may be repositioned to rotate with respect to the direction of the external electric field by agitating the cells in the flow-through chamber with a mechanical vibrator.

Alternatively, a rotating electric field can be generated by applying a multiple series of three-step pulses, wherein each successive three-step pulse generates an electric field with a different field orientation. Changes in field orientation produces a rotating electric field. Thus, molecules on either sides of the target cells can enter the cells and thereby improve the efficiency of the electroporation.

Such rotating electric fields can also be generated without specifically using a three-step pulse. A pulse having only one impulse step may also be used. A multiple series of this pulse can also generate a rotating electric field if the field orientation between each successive pulse in the series is changed.

Multiple pulses, e.g. multiple three-step pulses, can also be applied in each of different field orientations. Changes in field orientation between sets of multiple pulses can also produce a rotating electric field.

Moreover, the above rotating electric fields and the repositioning of the cells by a mechanical vibrator may be used in combination to improve the efficiency of electroporation.

The flow through chamber 100 can operate under a continuous flow mode or a batch mode, e.g. stop and go. During the continuous flow mode, liquid cell-molecule mixture is continuously fed into the flow through chamber while the rotating electric field is applied. In an ex vivo implementation, the time between the withdrawal of cells from a patient and reinfusion of electroporated cell may be long when cell culturing is performed before reinfusion. During the batch mode, the flow through chamber is first filled with a first volume of liquid cell-molecule mixture. The flow is then stopped and multiple series of three-step pulses is applied. Next, the flow through chamber is emptied and refilled with the second volume of liquid cell-molecule mixture.

Figure 4:
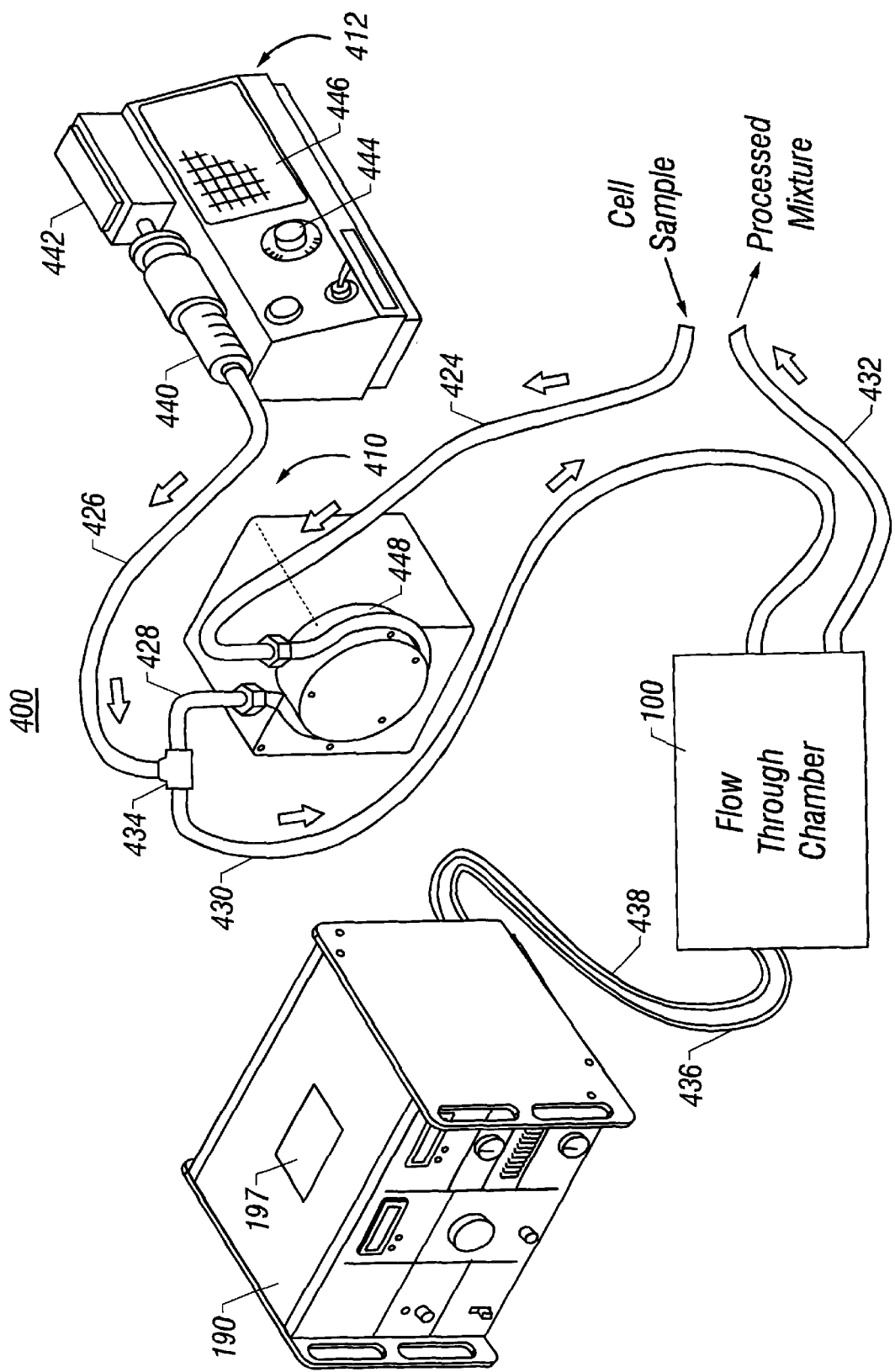
FIG. 4 illustrates a preferred embodiment of an apparatus for electroporation mediated, ex vivo, intra cellular drug and gene delivery.

The flow through chamber 100 can be used in an ex vivo implementation apparatus system 400 as shown in FIG. 4. This apparatus system 400 comprises a peristaltic pump 410, and an injection pump 412, a flow through chamber 100 and a signal generator 190. The apparatus 400 further comprises fluid conduit segments 424, 426, 428, 430 and 432 formed of a suitable tubing along with a T-shaped coupling 434 for enabling fluid flow in the directions indicated by the wide arrows in FIG. 4. The fluid conduit segment 424 directs a cell sample withdrawn from a patient (e.g., by using an implantable catheter) to the peristaltic pump 410. The cell sample may be directly withdrawn from the patient or may be cultured and processed for a certain period time. However obtained, the cell sample is mixed with a fluid medium from the injection pump 412 to form a mixture which is sent to the flow through chamber 100 via the fluid conduit segment 430 for electroporation. The fluid segment 432 connected to the flow through chamber 100 is used to infuse the electroporated mixture back to the patient by, for example, using an implantable catheter The apparatus 400 includes a pair of electric cables 436 and 438 for connecting the signal generator 190 and the flow through chamber 100.

The injection pump 412 may be of the conventional type that employs a syringe 440 for holding a quantity of a fluid medium carrying preselected macromolecules such as genes or pharmaceutical compounds. The plunger of the syringe 440 is pushed inwardly by a motor driven piston assembly 442. The rate of delivery of the fluid medium from the syringe 440 through the fluid conduit segment 426 may be adjusted via control dial 444 with the delivery parameters being indicated on a display 446.

The peristaltic pump 410 may be implemented by a conventional peristaltic pump and has controls for adjusting the rate of pumping. The peristaltic pump 410 actively pumps the liquid cell sample outside the patient 422 in a circulatory fashion. The peristaltic pump 410 includes a replaceable tubing segment 448 to propel the liquid cell sample therethrough to the T-shaped coupling 434 where the liquid cell sample mixes with the fluid medium from the injection pump 412. This fluid medium may be a pharmaceutical compound suspended in a suitable liquid vehicle such as saline solution. Where genes are to be introduced into the cells of the patient, the fluid medium comprises the genes suspended in a suitable liquid medium that will support the viability of the genes until they are inserted into the cells of the patient. Such fluid media are well known to those skilled in the art.

The details of the flow through chamber 100 are illustrated in FIGS. 1, 2A, and 2C. Electrical cables 436 and 438 from the signal generator 190 have plugs that are removably connected to the flow through chamber 100. These cables provide an electrical connection to the electrodes 150 of the flow through chamber 100.

The primary function of the electrical signal generating source 190 is to generate a predetermined electric signal which, when applied to the electrodes 150 of the flow through chamber 100, results in applying electric fields of a predetermined amplitude and duration to the mixture of liquid cell sample and fluid medium flowing therethrough.

When a cell is placed in an electrical field, an electrical potential is induced across the cell membrane. For a spherical cell, the membrane potential induced by an electrical field is:

$$V_m = 1.5 R E \cos \theta$$

where R is the radius of the cell, E is the strength of the external field and $\theta$ is the angle between the direction of the external field and the normal vector of the membrane at a the specific site. See U.S. Pat. No. 4,822,470, which is incorporated herein by reference.

The induced electric field within the membrane can be approximately represented by:

$$E_m = V_m/d = 1.5 (R/d) E \cos \theta$$

where d is the thickness of the membrane, and by definition is smaller than R. The electric field in the membrane exerts a strong force on the membrane, such that pores will be formed. The pores induced by the electric field are reversible, an introduction of molecules such as nucleic acid is possible, and most of the cells can remain viable when the strength of the applied electric field is properly chosen.

Preferably these fields are applied in a three step manner and the polarizations of the fields rotate in a predetermined sequence. Pairs of electrodes are connected together electrically and pulsed against another opposing pair of electrodes producing an electric field with a specific orientation. After one or several pulses, the pulse generator control 197 connects another pair of electrodes and pulses again. This produces an electric field with a different orientation from the first electric field produced.

Pulse generators for carrying out the method of the invention are and have been available on the market for a number of years. One suitable signal generator is the ELECTRO CELL MANIPULATOR Model ECM 600 commercially available from BTX, a division of Genetronics, Inc., of San Diego, Calif., U.S.A. The ECM 600 signal generator generates a pulse from the complete discharge of a capacitor which results in an exponentially decaying waveform. The electric signal generated by this signal generator is characterized by a fast rise time and an exponential tail. In the ECM 600 signal generator, the electroporation pulse length is set by selecting one of ten timing resistors marked R1 through R10. They are active in both High Voltage Mode (HVM) which has a capacitance fixed at about 50 microfarads and Low Voltage Mode (LVM) which has a capacitance ranging from about 25 to about 3,175 microfarads.

The application of an electrical field across the membrane of a cell induces transient pores which are critical to the electroporation process. The ECM 600 signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane makeup and individual characteristics of the cell wall itself. For example, mammalian cells typically require between 0.5 and 5.0 kV/cm before cell death and/or electroporation occurs. Generally, the required field strength varies inversely with the size of the cell.

The ECM 600 signal generator has a control knob that permits the adjustment of the amplitude of the set charging voltage applied to the internal capacitors from 50 to 500 volts in LVM and from 0.05 to 2.5 kV in HVM. The maximum amplitude of the electrical signal is shown on a display incorporated into the ECM 600 signal generator. This device further includes a plurality of push button switches for controlling pulse length, in the LVM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the outside electrodes in an automatic cycle that takes less than five seconds. The manual button may be sequentially pressed to repeatedly apply the predetermined electric field.

The waveform of the voltage pulse provided by the generator in the power pack can be in various forms. For certain applications, a square wave train may be preferably used as shown in FIG. 3B. FIGS. 3C–3F respectively show some other exemplary waveforms that may be used, including but not limited to, an exponentially decaying wave train, a unipolar oscillating pulse train, or a bipolar oscillating pulse train. In addition, a three-step pulse sequence may use different pulse waveforms for different steps.

The field strength of an electric impulse is calculated by dividing the voltage by the distance (in cm) between the electrodes. For example, if the voltage is 500 V between two electrode faces which are ½ cm apart, then the field strength is 500/(½) or 1000 V/cm or 1 kV/cm.

The waveform, electric field strength and pulse duration are dependent upon the exact construction of the delivery device and types of cells used in the electroporation procedure. One of skill in the art would readily be able to determine the appropriate number of pulses useful in the method of the invention by measuring transformation efficiency and cell survival using methods well known in the art.

The electrical pulse, preferably the three-step pulse, can be applied while the cells are at any temperature, generally the electrical pulse will be applied while the cells are at a temperature from about 2° C. to 39° C. Preferably, the electrical pulse is applied while the cells are at about 2° C. to 10° C. The temperature is not changed during a single three-step pulse. Rather, if temperature change is desired, the temperature change is imposed after completion of one three-step pulse sequence and before the start of another three-step pulse sequence. Following the electrical pulse, the cells can be incubated for a period of time. Preferably, the cells are incubated at a temperature of about 37° C.

Figure 5:
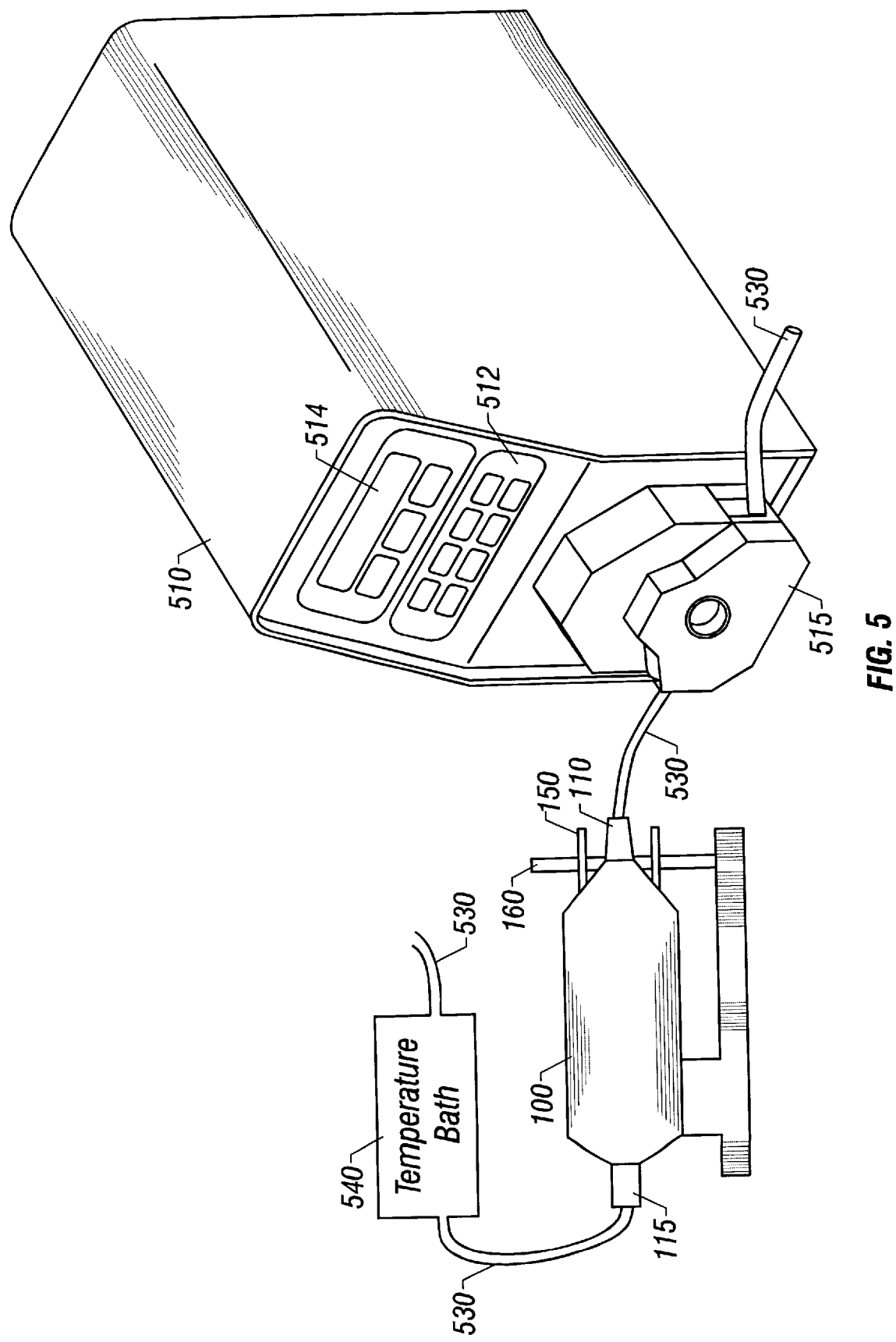
FIG. 5 is a perspective view of an alternate embodiment of pump and flow through chamber component having variable temperature baths.

FIG. 5 shows an alternative embodiment of a combination peristaltic pump 510 and a flow through chamber 100 with multiple temperature baths connected in the fluid conduit 530. The peristaltic pump 510 has a rotor assembly 515 for receiving tubing 530. A control panel 512 provides means for selection and control of various parameters of the pump 510, including start-stop directional pumping and rate of pumping and time. The pump 510 is also provided with a suitable display panel 514 providing a visual readout of certain selected parameters or operating conditions. One embodiment of the flow through chamber 100 is illustrated in FIGS. 1, 2A, and 2C. The flow through chamber 100 provides the multiple electrical pulses which generates a rotating electric field. After each pulse the mixture of cells and molecules is pumped to a specified temperature bath 540. The apparatus provides a means to pulse the mixture at varying temperatures and allows the mixture to reside in a different temperature bath after the pulse is applied.

Figure 6:
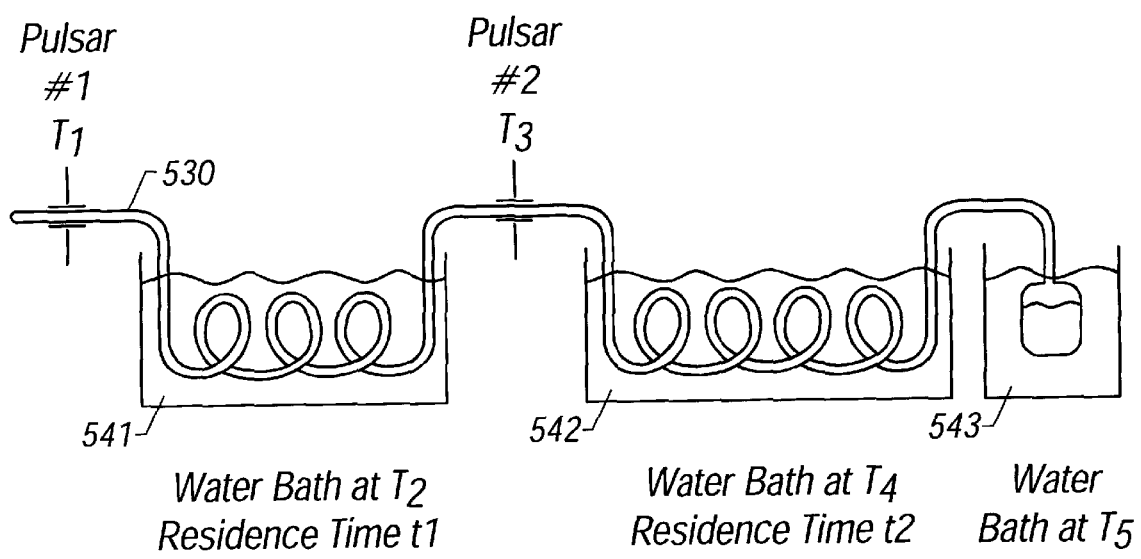
FIG. 6 is a detail schematic of the embodiment illustrated in FIG. 5 during operation.

FIG. 6 shows a diagram of one preferred process of temperature variation after each pulsing event. A pulsing event may be one single three-step pulse or a series of three-step pulses. A first pulsing event 610 occurs in a flow through chamber 100. The mixture is pumped through tubing 530 into a first temperature bath 541 for the cells to recover. After a second pulsing event, the mixture is pumped into a second temperature bath 542 for a second recovery. After a third temperature bath 543 can be used to provide cell culturing or other activities depending on the specific protocol used.

The following example is intended to illustrate but not limit the invention. While they are typical of those that might be used, other procedures known to those skilled in the art may alternatively be used. One sample protocol for electroporation of human red blood cells is provided. The First pulsing event occurs at 4° C. The electric field strength generated is about 2500 Volts per centimeter while the pulsing event lasts for about 0.3 milliseconds. The cells are allowed to recover at about 4° C. for approximately 5 minutes. A second pulsing event occurs at about 37 degrees Celsius. The electric field strength generated is about 1875 Volts per centimeter while the pulsing event lasts for about 0.3 milliseconds. The cells are allowed to recover at about 37° C. for approximately 10 minutes. The electroporated cells are then accumulated at another water bath at about 4° C.

Figure 7:
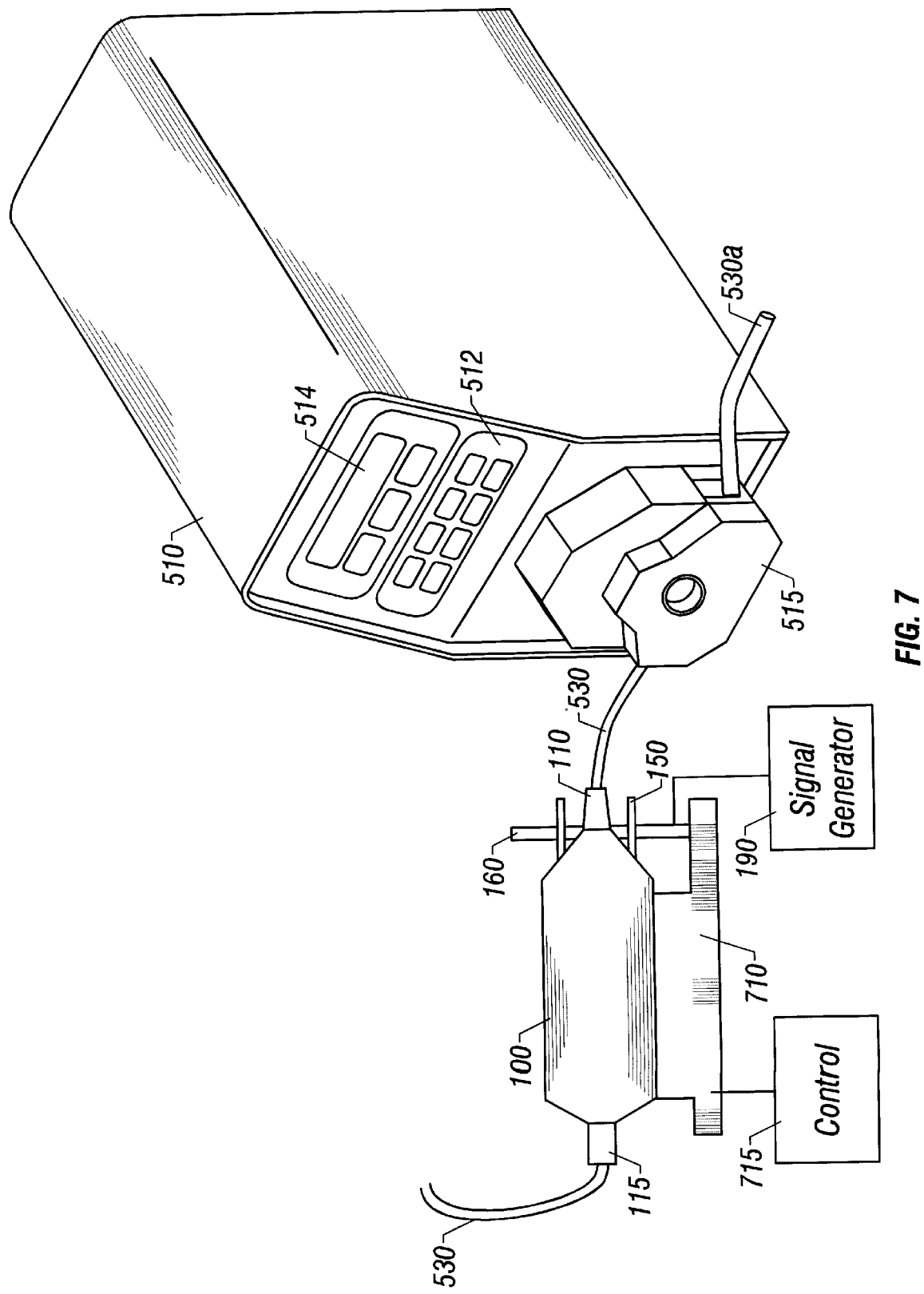
FIG. 7 is a perspective view of another alternate embodiment of a pump and flow through chamber mounted on a vibrating table.

FIG. 7 shows another embodiment where the flow through chamber 100 is mounted on a vibrating table 710. The vibrating table 710 produces vibrate the flow through chamber 100 to mechanically agitate the cell-molecule mixture between successive pulses, e.g. successive three-step pulses. This repositions cells and can potentially increase the areas of permeabilization to improve the electroporation efficiency. The degree and duration of the vibration can be adjusted by a control means 715 which is coupled to the vibrating table 710. The degree of the vibration should be sufficient to slightly turn the cells' orientation to the electrodes.

A number of embodiments of the present invention have been described. Nevertheless, it will be understood that various modifications and enhancements may be made without departing from the spirit and scope of the invention as defined by the following claims.

What is claimed is:

1. A method for introducing molecules into a living cell, comprising:

contacting the living cell with selected molecules to form a cell-molecule mixture, wherein the cell-molecule mixture is maintained at a first specified temperature;

exposing the cell-molecule mixture to a first electric impulse to effect a collection of the selected molecules at a cell membrane of the cell;

exposing the cell-molecule mixture to a second electric impulse after the first electric impulse to cause transient permeabilization of the cell membrane; and exposing the cell-molecule mixture to a third electric impulse after the second electric impulse transport a portion of the selected molecules through the cell membrane into the cell;

wherein the first, second, and third electric impulses form one single three-step pulse and the three-step pulse is applied repeatedly to the cell-molecule mixture with the electric field in different directions to generate a rotating electric field.

2. The method of claim 1, further comprising repositioning the living cells after each successive three-step pulse by mechanically agitating the cell-molecule mixture.

3. The method of claim 1, wherein the steps are carried out ex vivo.

4. The method of claim 1, wherein the first and third electric impulses each have a duration from about 0.1 to about 1000 milliseconds.

5. The method of claim 1, wherein the second electric impulse has a duration from about 1 to about 1000 microseconds.

6. The method of claim 1, wherein the first and third electric impulses each create an electric field of about from 10 to 1000 Volts per centimeter.

7. The method of claim 1, wherein the second electric impulse creates an electric field of about from 100 to 10,000 Volts per centimeter.

8. The method of claim 1, wherein the first, second, and third electric impulses are comprised of a square wave pulse train, an exponentially decaying wave pulse train, a unipolar oscillating wave pulse train, or a bipolar oscillating wave pulse train.

9. A continuous flow method for implanting molecules into living cells of a patient, comprising:

providing an elongated flow through a chamber having an inlet and an outlet and more than two electrodes spaced apart in a specified configuration disposed between the inlet and the outlet;

withdrawing a cell sample from a patient;

passing the cell sample in a fluid through the flow through chamber between the electrodes and returning the cell sample to the patient;

injecting a predetermined quantity of a fluid medium carrying preselected molecules into the cell sample after the cell sample has been drawn from the patient and before the cell sample passes through the flow through chamber, forming a mixture of the fluid medium and the cell sample;

maintaining the mixture at a first specified temperature;

executing a pulsing event by producing a predetermined electric signal or series of electric signals to the electrodes so as to apply electric fields of predetermined amplitudes and durations to the flow of the mixture of the fluid medium and the cell sample;

maintaining the mixture at a second specified temperature, wherein the second specified temperature is different than the first specified temperature; and repeatedly applying another pulsing event.

10. The method of claim 9, further comprising maintaining the mixture at another specified temperature after the pulsing event at the second specified temperature.

11. A continuous flow method for implanting molecules into living cells of a patient, comprising:

providing an elongated flow through chamber having an inlet and an outlet and more than two electrodes spaced apart in a specified configuration disposed between the inlet and the outlet;

withdrawing a cell sample from a patient;

passing the cell sample in a liquid through the flow through chamber between the electrodes and returning the liquid cell sample to the patient;

injecting a predetermined quantity of a fluid medium carrying preselected molecules into the cell sample after the cell sample has been drawn from the patient and before the cell sample passes through the flow through chamber, forming a mixture of the fluid medium and the cell sample;

maintaining the mixture at a first specified temperature;

applying a predetermined electric pulse or series of electric pulses to the electrodes for generating and applying electric fields in a first field orientation of predetermined amplitudes and durations to the flow of the mixture of the fluid medium and the cell sample; and repeating the step of applying a predetermined electric pulse or series of electric pulses to the electrodes in a different electric field orientation to produce a rotating electric field to the mixture.

12. The method as in claim 11, wherein each pulse is a three-step pulse sequentially comprising a first electrical impulse, a second electrical impulse, and a third electrical impulse.

13. The method of claim 12, wherein the first and second electric impulses each have a duration of about 0.1 to 1000 milliseconds.

14. The method of claim 12, wherein the second electric impulse has a duration of about 1 to 1000 microseconds.

15. The method of claim 12, wherein the first and second electric impulses each create an electric field of about 10 to 1000 Volts per centimeter.

16. The method of claim 12, wherein the second electric impulse creates an electric field of about 100 to 10,000 Volts per centimeter.

17. The method of claim 12, wherein the first, second, and third electric impulses are comprised of a square wave pulse train, an exponentially decaying wave pulse train, a unipolar oscillating wave pulse train, or a bipolar oscillating wave pulse train.

18. The method of claim 11, wherein the electrodes are linear.

19. The method of claim 11, wherein the flow through chamber has four linear electrodes forming a square configuration.

20. The method of claim 11, wherein the flow through chamber has six linear electrodes forming a hexagonal configuration.

21. The method of claim 11, wherein the flow through chamber has a circular cross section and the more than two electrodes are arranged with respect to one another in a circular configuration.

22. The method of claim 11, further comprising repositioning the cells in the mixture between successive pulses by mechanically vibrating the flow through chamber.

23. The method of claim 11, wherein the flow through chamber uses detachable contacts in a printed circuit board template to provide electrical signals to the electrodes.

24. A method for implanting molecules into living cells of a patient, comprising:

providing an elongated flow through chamber having an inlet and an outlet and more than two electrodes spaced apart in a specified configuration disposed between the inlet and the outlet for fluid to flow between;

withdrawing a cell sample from a patient;

injecting a predetermined quantity of a fluid medium carrying preselected molecules into the cell sample in a liquid after the cell sample has been drawn from the patient forming a cell-molecule mixture;

filling the cell-molecule mixture into the flow through chamber between the electrodes;

maintaining the mixture at a first specified temperature;

first applying a predetermined electric pulse or series of electric pulses of a predetermined amplitude and duration to the electrodes for generating and applying electric fields of a predetermined amplitude and duration to the flow of the cell-molecule mixture, wherein each applying forms a first pulsing event that generates an electric field with a first field orientation;

repeatedly applying a successive pulsing event, wherein the successive pulsing event has a different electric field orientation than the first pulsing event, thereby generating a rotating electric field;

emptying the flow through chamber; and second filling another volume of cell-molecule mixture into the flow through chamber.

25. An apparatus for introducing molecules into living cells of a patient, comprising:

a housing including an elongated flow through chamber having an inlet and an outlet to form a fluid conduit;

more than two electrodes positioned in the housing and spaced apart in a specified configuration for generating rotating electric fields and disposed between the inlet and the outlet for fluid to flow therebetween;

means for withdrawing a cell sample from a patient;

means for passing the cell sample in a liquid through the flow through chamber between the electrodes and returning the cell sample to the patient;

means for injecting a predetermined quantity of a fluid medium carrying preselected molecules into the cell sample after the cell sample has been drawn from the patient and before the cell sample passes through the flow through chamber; and a signal source connected to supply electrical energy to the electrodes to apply a multiple series of electric pulses of different field orientations to the mixture of liquid cell sample and fluid medium, the electric pulses configured to make the walls of preselected cells in the liquid cell sample transiently permeable to permit molecules to enter the preselected cells without killing the cells.

26. The apparatus of claim 25, wherein the electrodes are linear rods positioned at each corner along the length of the housing.

27. The apparatus of claim 25, wherein the flow through chamber has four electrodes forming a square configuration for generating four different electric field orientations.

28. The apparatus of claim 25, wherein the flow through chamber has six electrodes forming a hexagonal configuration for generating six different electric field orientations.

29. The method of claim 25, wherein the flow through chamber has a circular cross section and the more than two electrodes are arranged with respect to one another in a circular configuration.

30. The apparatus of claim 25, further comprising a mechanical vibrating element engaged to the house and configured to mechanically agitate the cells between successive electrical pulses cause repositioning of the cells.

31. The apparatus of claim 30, wherein the mechanical vibrating element includes a vibrating table mounted to the flow through chamber.

32. The apparatus of claim 25, wherein the electrodes are removably attached to a printed circuit board template which provides an electrical connection between the electrodes and the signal source.

33. The apparatus of claim 25, further comprising multiple temperature baths in order to pulse cells at different temperatures and then after pulsing let the cells recover for specified residence time at another temperature.

34. A device for introducing transient pores into living cells, comprising:

a housing including a chamber having an inlet and an outlet;

a plurality of electrodes positioned in the house to provide a rotating electric field within the chamber;

means for introducing a mixture of a fluid medium carrying preselected molecules and a liquid cell sample into the inlet of the housing; and means for applying a predetermined electric signal of a predetermined amplitude and duration to the electrodes and repeatedly applying rotating electric fields of a predetermined amplitude and duration to the mixture of the fluid medium and the liquid cell sample in such a way to make the walls of preselected cells in the liquid cell sample transiently permeable to permit certain molecules to enter the preselected cells without killing the cells.

* * * * *